US006452054B2

(12) United States Patent
Aronhime et al.

(10) Patent No.: US 6,452,054 B2
(45) Date of Patent: Sep. 17, 2002

(54) SERTRALINE HYDROCHLORIDE POLYMORPHS, PROCESSES FOR PREPARING THEM, COMPOSITIONS CONTAINING THEM AND METHODS OF USING THEM

(75) Inventors: Judith Aronhime; Marioara Mendelovici, both of Rehovot; Tamar Nidam, Yahud; Claude Singer, Kfar Saba, all of (IL)

(73) Assignee: Teva Pharmaceutical Industries Ltd., Petah Tiqva (IL)

( * ) Notice: Subject to any disclaimer, the term of this patent is extended or adjusted under 35 U.S.C. 154(b) by 0 days.

(21) Appl. No.: 09/746,320

(22) Filed: Dec. 21, 2000

Related U.S. Application Data

(60) Provisional application No. 60/190,603, filed on Mar. 20, 2000, provisional application No. 60/187,910, filed on Mar. 8, 2000, provisional application No. 60/187,336, filed on Mar. 6, 2000, and provisional application No. 60/171,341, filed on Dec. 21, 1999.

(51) Int. Cl.$^7$ ............................................. C07C 211/00
(52) U.S. Cl. ........................ 564/308; 564/428; 514/647; 514/657
(58) Field of Search ................................ 564/308, 428; 514/647, 657

(56) References Cited

U.S. PATENT DOCUMENTS

| | | | |
|---|---|---|---|
| 4,536,518 A | | 8/1985 | Welch, Jr. et al. |
| 5,082,970 A | | 1/1992 | Braish |
| 5,248,699 A | * | 9/1993 | Sysko et al. |
| 5,463,126 A | | 10/1995 | Williams |
| 5,734,083 A | * | 3/1998 | Wilson et al. |

FOREIGN PATENT DOCUMENTS

| | | |
|---|---|---|
| JP | 2000-26378 | 1/2000 |
| JP | 2000-26379 | 1/2000 |
| WO | WO 99/47486 | 9/1999 |

OTHER PUBLICATIONS

G.M. Wall, "Pharmaceutical Applications of Drug Crystal Studies", *Pharmaceutical Manufacturing*, vol. 3, No. 2, pp. 33–42, Feb. 1986.

J.K. Haleblian and W. McCrone, "*Pharmaceutical Applications of Polymorphism*" *Journal of Pharmaceutical Sciences*, vol. 58, No. 8, pp. 911–929, Aug. 1969.

J.K. Haleblian, "Characterization of Habits and Crystalline Modification of Solids and Their Pharmaceutical Applications", *Journal of Pharmaceutical Sciences*, vol. 64, No. 8, pp. 1269–1288, Jul. 1975.

Welch, et al., "*Nontriczclic Antidepressant Agents Derived from cis–and trans–1–Amino–4–arylteralins*", *Journal of Medicinal Chemistry*, vol. 27, No. 11, pp. 1508–1515, Feb. 14, 1984.

U.S. patent application Ser. No. 09/448,985, filed Nov. 24, 1999, "Sertraline Hydrochloride Polymorphs," E. Schwartz et al.

* cited by examiner

*Primary Examiner*—Samuel Barts
(74) *Attorney, Agent, or Firm*—Kenyon & Kenyon

(57) ABSTRACT

The present invention is directed to novel polymorphic Forms XI, XII, XIII, XIV, XV and XVI of sertraline hydrochloride, to processes for preparing them, methods of using them to treat disease, methods of using them to make other sertraline hydrochloride forms, and to pharmaceutical dosages containing the novel forms.

74 Claims, 7 Drawing Sheets

SERTRALINE HYDROCHLORIDE POLYMORPHS, PROCESSES FOR PREPARING THEM, COMPOSITIONS CONTAINING THEM AND METHODS OF USING THEM

CROSS-REFERENCE TO RELATED APPLICATIONS

This application claims the benefit of provisional applications serial Nos. 60/171,341, filed Dec. 21, 1999; 60/187,336, filed Mar. 6, 2000; 60/187,910, filed Mar. 8, 2000; and 60/190,603, filed Mar. 20, 2000. All four provisional applications are incorporated by reference. Co-pending commonly assigned U.S. Application Ser. No.: 09/448,985, filed Nov. 24, 1999, is incorporated herein by reference.

FIELD OF THE INVENTION

The present invention relates to novel polymorphic Forms XI, XII, XIII, XIV, XV and XVI of sertraline hydrochloride, to processes for preparing them, methods of using them to treat disease, methods of using them to make other sertraline hydrochloride forms, and to pharmaceutical dosages containing the novel forms.

BACKGROUND OF THE INVENTION

Sertraline hydrochloride, (1S-cis)-4-(3,4 dichlorophenyl)-1,2,3,4-tetrahydro-N-methyl-1-naphthalenamine hydrochloride, having the formula

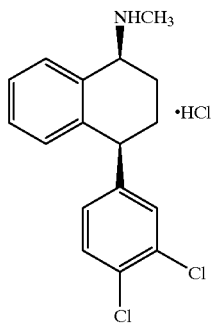

is approved, under the trademark Zoloft®, by the U.S. Food and Drug Administration, for the treatment of depression, obsessive-compulsive disorder and panic disorder.

U.S. Pat. No. 4,536,518 ("the '518 patent") describes the preparation of sertraline hydrochloride with a melting point of 243–245° C. by treating an ethyl acetate/ether solution of the free base with gaseous hydrogen chloride. The solid state properties of the sertraline hydrochloride so produced are not otherwise disclosed.

According to U.S. Pat. No. 5,248,699 ("the '699 patent"), the sertraline hydrochloride produced by the method of the '518 patent has a crystalline form denominated "Form II." The '699 patent discloses four other polymorphs designated Forms I, III, IV, and V.

The present invention includes new polymorphic forms of sertraline hydrochloride. Polymorphic forms of a compound can be distinguished in a laboratory by X-ray diffraction spectroscopy and by other methods such as, infrared spectrometry. It is desirable to investigate all solid state forms of a drug, including all polymorphic forms, and to determine the stability, dissolution and flow properties of each polymorphic form. For a general review of polymorphs and the pharmaceutical applications of polymorphs see G. M. Wall, *Pharm Manuf.* 3, 33 (1986); J. K. Haleblian and W. McCrone, *J. Pharm. Sci.*, 58, 911 (1969); and J. K. Haleblian, *J. Pharm. Sci.*, 64, 1269 (1975), all of which are incorporated herein by reference.

Commonly-assigned, co-pending U.S. patent application Ser. No. 09/448,985 filed Nov. 24, 1999, which is incorporated herein by reference, discloses novel methods of making sertraline hydrochloride Form V that were discovered after unsuccessful attempts at sublimation. One of the methods disclosed in that application involves crystallization from an acidic hexane and/or isopropanol solvent system that can be made acidic by addition of concentrated hydrochloric acid in lieu of gaseous hydrochloric acid. The co-pending application also discloses other new sertraline hydrochloride forms that have been designated Forms VI, VII, VIII, IX and X.

SUMMARY OF THE INVENTION

The present invention relates to novel forms of sertraline hydrochloride. The present invention provides processes for preparing sertraline hydrochloride Forms XI, Form XII, Form XIII, Form IV, Form XV and Form XVI; compositions containing sertraline hydrochloride Forms XI–XVI; methods of using sertraline hydrochloride Forms XI–XVI to prepare other forms of sertraline hydrochloride and methods of using sertraline hydrochloride Forms XI–XVI to treat depression, obsessive-compulsive disorder and panic disorder.

The present invention relates to sertraline hydrochloride Form XI which is characterized by a powder X-ray diffraction pattern comprising peaks at about 16.0±0.2, 17.7±0.2, 20.7±0.2, 24.9±0.2 and 29.2±0.2 degrees two-theta. Sertraline hydrochloride Form XI of the present invention is also characterized by an infrared spectrum comprising absorption bands at 739, 1040, 1201, 1560 and 1595 $cm_{-1}$.

The present invention also relates to a process for making sertraline hydrochloride Form XI comprising the steps of: (a) dissolving sertraline hydrochloride in benzyl alcohol to form a sertraline hydrochloride solution; (b) crystallizing sertraline hydrochloride Form XI from the sertraline hydrochloride solution; and (c) isolating the sertraline hydrochloride Form XI.

The present invention also relates to sertraline hydrochloride Form XI where sertraline hydrochloride Form XI is sertraline hydrochloride Form XI benzyl alcohol solvate.

The present intention also relates to sertraline hydrochloride Form XI benzyl alcohol hemi-solvate, sertraline hydrochloride Form XI benzyl alcohol mono-solvate, sertraline hydrochloride Form XI benzyl alcohol di-solvate and sertraline hydrochloride Form XI benzyl alcohol tri-solvate.

The present invention also relates to a method of making sertraline hydrochloride Form X comprising the step of heating sertraline hydrochloride Form XI.

The present invention also relates to sertraline hydrochloride Form XII which is characterized by a powder X-ray diffraction pattern comprising peaks at about 4.3±0.2, 12.0±0.2, 13.4±0.2, 16.3±0.2, and 17.4±0.2 degrees two-theta.

The present invention also relates to a process for making sertraline hydrochloride Form XII comprising the steps of: (a) exposing sertraline hydrochloride to water vapor; and (b) isolating sertraline hydrochloride Form XII. In another embodiment of the invention, the process for making sertraline hydrochloride Form XII comprises the steps of: (a) exposing sertraline hydrochloride Form V to water vapor; and (b) isolating sertraline hydrochloride Form XII. The present invention also relates to sertraline hydrochloride Form XII hydrates, including sertraline hydrochloride Form XII mono-hydrate.

The present invention also relates to sertraline hydrochloride Form XIV which is characterized by a powder x-ray diffraction pattern comprising peaks at about 7.4±0.2, 9.6±0.2, 12.0±0.2, 12.8±0.2, 14.3±0.2, 16.0±0.2, 16.2±0.2, 18.0±0.2, 21.1±0.2, 23.2±0.2, 23.6±0.2, 24.3±0.2, 24.9±0.2, 25.7±0.2, 26.7±0.2, 29.6±0.2 and 32.5±0.2 degree two-theta.

The present invention also relates to a process for making sertraline hydrochloride Form XIV comprising the steps of: (a) dissolving sertraline base in a solvent mixture of methanol and hexane to form a solution of sertraline base and the solvent; (b) adding hydrogen chloride to the solution to attain a pH of from about 0.5 to about 1.5; (c) precipitating sertraline hydrochloride from the solution; (d) removing the solvent; and (e) isolating sertraline hydrochloride Form XIV.

The present invention also relates to a process for making sertraline hydrochloride Form XIV comprising the steps of: (a) adding sertraline hydrochloride Form II to methanol to form a suspension of solid sertraline hydrochloride in methanol; and (b) isolating sertraline hydrochloride Form XIV.

The present invention also relates to a process for making sertraline hydrochloride Form V comprising the steps of: (a) heating sertraline hydrochloride Form XIV; and (b) isolating sertraline hydrochloride Form V.

The present invention also relates to sertraline hydrochloride Form XIII which is characterized by a powder X-ray diffraction pattern comprising peaks at about 8.5±0.2, 13.3±0.2, 14.0±0.2, 15.3±0.2, 16.3±0.2, 17.5±0.2, 20.1±0.2, 21.5±0.2, 22.5±0.2, 23.6±0.2, 25.0±0.2 and 25.9±0.2 degrees two-theta.

The present invention also relates to a process for making sertraline hydrochloride Form XIII comprising the steps of: (a) heating sertraline hydrochloride Form XIV; and (b) isolating sertraline hydrochloride Form XIII.

The present invention also relates to a process for making sertraline hydrochloride Form V comprising the steps of: (a) heating sertraline hydrochloride Form XIII; and (b) isolating sertraline hydrochloride Form V.

The present invention also relates to sertraline hydrochloride Form XV which is characterized by a powder x-ray diffraction pattern comprising peaks at about 6.5±0.2, 10.7±0.2, 12.9±0.2, 14.2±0.2, 15.2±0.2, 16.6±0.2, 17.5±0.2, 18.1±0.2, 19.9±0.2, 20.4±0.2 24.0±0.2 and 24.5±0.2 degrees two-theta.

The present invention also relates to a process for making sertraline hydrochloride Form XV comprising the steps of: (a) dissolving sertraline base in a solvent comprising a mixture of isopropanol and a non-polar solvent to form a solution of sertraline base; (b) adding aqueous hydrochloric acid to the solution of sertraline base to facilitate precipitation of sertraline hydrochloride Form XV; (c) removing the solvent; and (d) isolating sertraline hydrochloride Form XV. Preferably, the non-polar solvent is hexane.

The present invention also relates to a process for making sertraline hydrochloride Form XV comprising the steps of: (a) adding sertraline base to isopropanol; (b) adding aqueous hydrochloric acid to the mixture of sertraline base and isopropanol in an amount sufficient to form sertraline hydrochloride; (c) heating the mixture of sertraline hydrochloride and isopropanol to facilitate complete dissolution of sertraline hydrochloride; (d) adding water to the mixture to facilitate complete dissolution of sertraline hydrochloride; (e) stirring the mixture for a time sufficient to induce the transformation to sertraline hydrochloride Form XV; and (f) isolating sertraline hydrochloride Form XV.

The present invention also relates to a process for making sertraline hydrochloride Form V comprising the steps of: (a) heating sertraline hydrochloride Form XV; and (b) recovering sertraline hydrochloride Form V.

The present invention also relates to sertraline hydrochloride Form XVI which is characterized by a powder X-ray diffraction pattern comprising peaks at about 15.6±0.2, and 23.0°±0.2° degrees two-theta.

The present invention also relates to a process for preparing sertraline hydrochloride Form XVI comprising the steps of: (a) dissolving sertraline base in a solvent wherein the solvent is selected from the group consisting of hexane, cyclohexane and toluene to form a mixture of sertraline base and the solvent; (b) adding hydrogen chloride to the mixture to attain a pH of from about 1 to about 1.5; (c) precipitating sertraline hydrochloride Form XVI from the mixture; (d) removing the solvent; and (e) isolating sertraline hydrochloride Form XVI.

The present invention also relates to processes for preparing sertraline hydrochloride Form II comprising the steps of: (a) adding sertraline hydrochloride Form XIV to a solvent selected from the group consisting of ethyl acetate, acetone, and t-butyl-methyl-ether to form a suspension of sertraline hydrochloride; (b) heating the suspension; (c) stirring the suspension for a time sufficient to transform sertraline hydrochloride Form XIV to sertraline hydrochloride Form II; and (d) isolating sertraline hydrochloride Form II. Preferably, by these methods, the suspension is heated to a temperature range of about 25° C. to reflux, and more preferably the suspension is heated to reflux. The process further comprises the step of cooling the suspension prior to isolating sertraline hydrochloride Form II.

The present invention also relates to processes for preparing sertraline hydrochloride Form II comprising the steps of: (a) adding sertraline hydrochloride Form XV to a solvent selected from the group consisting of ethyl acetate, acetone, t-butyl-methyl-ether and cyclohexane to form a suspension of sertraline hydrochloride; (b) stirring the suspension for a time sufficient to transform sertraline hydrochloride Form XV to sertraline hydrochloride Form II; (c) heating the suspension; and (d) isolating sertraline hydrochloride Form II. Preferably, by these methods, the suspension is heated to a temperature range of about 25° C. to reflux, more preferably, the suspension is heated to reflux. The process further comprises the step of cooling the suspension prior to isolating sertraline hydrochloride Form II. Preferably, the suspension is cooled to a temperature range of about 25° C. to about 5° C.

The present invention also relates to a process for preparing sertraline hydrochloride Form II comprising the steps of: (a) adding sertraline hydrochloride Form XVI to a solvent selected from the group consisting of ethyl acetate and acetone to form a suspension of sertraline hydrochloride; (b) heating the suspension to facilitate the transformation for sertraline hydrochloride Form XVI to sertraline hydrochloride Form II; and (c) isolating sertraline hydrochloride Form II.

The present invention also relates to a pharmaceutical composition comprising a therapeutically effective amount of sertraline hydrochloride selected from the group consisting of: sertraline hydrochloride Form XI, Form XII, Form XIII, Form XIV, Form XV, Form XVI, and mixtures thereof, and a pharmaceutically acceptable vehicle.

The present invention also relates to a method for treating depression comprising the step of administering to a patient in need of such treatment a therapeutically effective amount of sertraline hydrochloride selected from the group consisting of: sertraline hydrochloride Form XI, Form XII, Form XIII, Form XIV, Form XV, Form XVI, and mixtures thereof.

The present invention also relates to a method for treating obsessive-compulsive disorder comprising the step of administering to a patient in need of such treatment a therapeutically effective amount of sertraline hydrochloride selected from the group consisting of: sertraline hydrochloride Form XI, Form XII, Form XIII, Form XIV, Form XV, Form XVI, and mixtures thereof.

The present invention also relates to a method for treating panic disorder comprising the step of administering to a patient in need of such treatment a therapeutically effective amount of sertraline hydrochloride selected from the group consisting of: sertraline hydrochloride Form XI, Form XII, Form XIII, Form XIV, Form XV, Form XVI, and mixtures thereof.

Sertraline hydrochloride Form XI, Form XII, Form XII, Form XIV, Form XV and Form XVI are useful in the preparation of pharmaceutical compositions which are particularly useful for treatment of depression, obsessive-compulsive disorder and panic disorder.

Sertraline hydrochloride Form XI has the advantage of providing the preservative, benzyl alcohol, and sertraline hydrochloride in the same step and has the advantage of simplifying the formulation process by omitting a separate addition step and potentially more accurately controlling the quantity of benzyl alcohol since a larger quantity of material is measured than when the preservative is added separatively.

Sertraline hydrochloride Form XIV, Form XV and Form XVI are useful for preparing sertraline hydrochloride Form II.

Sertraline hydrochloride Form XIV and Form XV are useful for preparing sertraline hydrochloride Form V.

DETAILED DESCRIPTION OF THE INVENTION

The present invention provides; processes for preparing sertraline hydrochloride Forms XI, Form XII, Form XIII, Form XIV, Form XV and Form XVI; compositions containing sertraline hydrochloride Forms XI–XVI; methods of using sertraline hydrochloride Forms XI–XVI to prepare other forms of sertraline hydrochloride and methods of using sertraline hydrochloride Forms XI–XVI to treat depression, obsessive-compulsive disorder and panic disorder.

Sertraline Hydrochloride Form XI

One embodiment of the present invention provides the sertraline hydrochloride Form XI. Sertraline hydrochloride Form XI is a benzyl alcohol hemi-solvate of formula I:

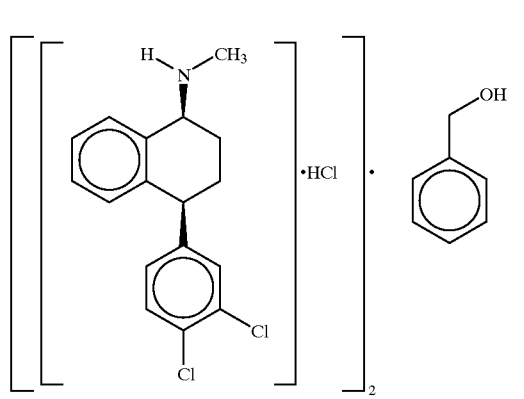

The invention further provides a method of obtaining sertraline hydrochloride Form XI by crystallization of sertraline hydrochloride from benzyl alcohol. Although benzyl alcohol may be toxic in large quantities, its administration in dosages contemplated by the present invention is generally pharmaceutically acceptable. Benzyl alcohol is a known antimicrobial preservative and thus provides compositions containing benzyl/alcohol with improved shelf life against bacteria, mold, fungus and yeast.

Figure 1:
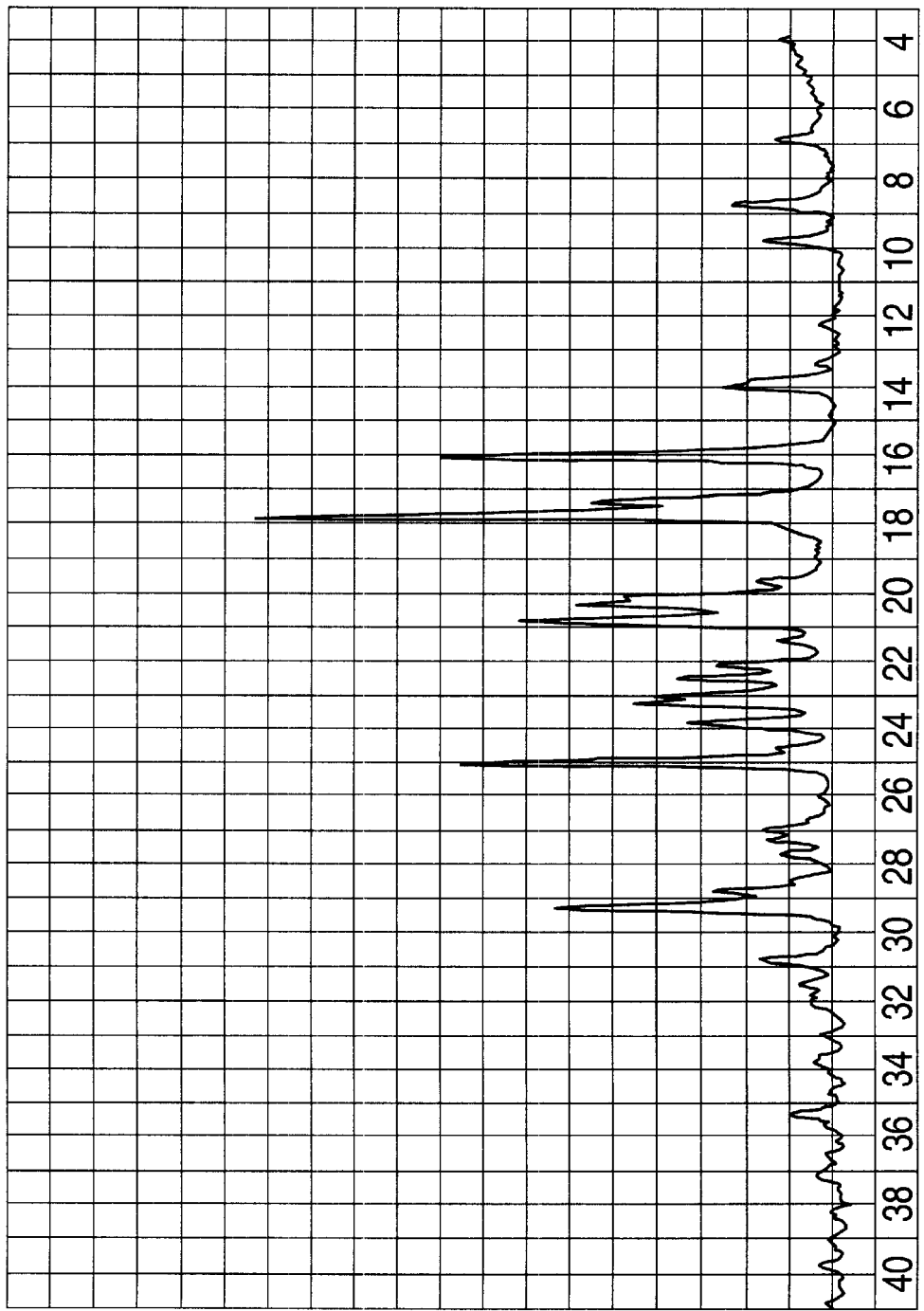
FIG. 1 is a characteristic powder X-ray diffraction pattern of sertraline hydrochloride Form XI.
Figure 2:
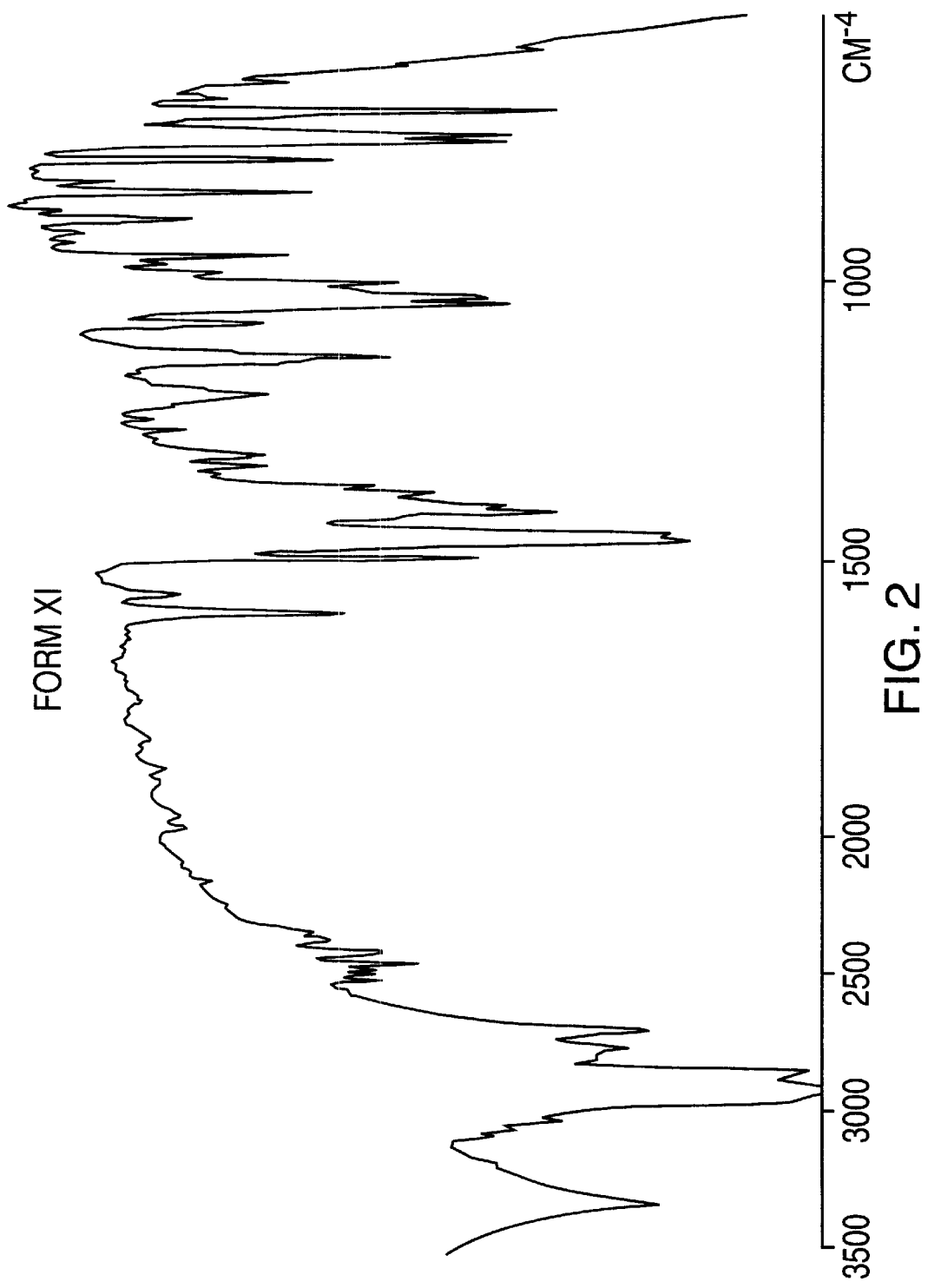
FIG. 2 is a characteristic infrared absorption spectrum of sertraline hydrochloride Form XI.

Sertraline hydrochloride Form XI is characterized by its powder X-ray diffraction pattern which exhibits characteristic reflections at about 6.9±0.2, 8.7±0.2, 9.7±0.2, 14.0±0.2, 16.0±0.2, 17.3±0.2, 17.7±0.2, 20.3±0.2, 20.7±0.2, 22.1±0.2, 22.5±0.2, 23.0±0.2, 23.8±0.2, 24.9±0.2, and 29.2±0.2 degrees two-theta, as shown in FIG. 1. The infrared absorption spectrum of sertraline hydrochloride Form XI has absorption bands at 698, 739, 750, 781, 817, 838, 886, 954, 1001, 1030, 1040, 1075, 1134, 1201, 1312, 1328, 1493, 1560, and 1595 cm$^{-1}$, as shown in FIG. 2.

Sertraline hydrochloride Form XI is prepared by dissolving sertraline hydrochloride in benzyl alcohol. Since, by the methods of the present invention, the starting material sertraline hydrochloride is completely dissolved, any form of sertraline hydrochloride may be used, including, but not limited to sertraline hydrochloride Forms I–X, XII–XVI and amorphous sertraline hydrochloride. Preferably, the concentration of sertraline hydrochloride, after it has completely dissolved in benzyl alcohol, is about 0.5 M or greater. The concentration should not be so high that the sertraline hydrochloride does not completely dissolve in a reasonable amount of time at 100° C. To obtain the benzyl alcohol hemi-solvate, sertraline hydrochloride Form XI, the concentration should be preferably about 1M. While we have obtained sertraline hydrochloride Form XI as the benzyl alcohol hemi-solvate, higher solvates like mono-solvates, di-solvates and tri-solvates may also be obtainable by this method. Mono-solvates have a crystal structure containing one solvent molecule per molecule of sertraline hydrochloride. Di-solvates have two molecules of solvent per sertraline hydrochloride and tri-solvates have three.

It may be necessary to heat the benzyl alcohol or sertraline hydrochloride/benzyl alcohol mixture in order to facilitate dissolution of sertraline hydrochloride. The preferred elevated temperature is 100° C. when heating is used.

After complete dissolution of the sertraline hydrochloride, crystallization of sertraline hydrochloride Form XI may be induced by cooling from the elevated temperature. In order to produce homogeneous solvate crystals, crystal growth should be slow and so the cooling likewise should be conducted slowly. To produce the sertraline hydrochloride Form XI hemi-solvate selectively and homogeneously, the solution is preferably cooled at a rate of about 38° C. h$^{-1}$ or less. When the preferred concentration range is used, cooling to about room temperature should produce the solvate in good yield without any further cooling being required. The choice to further cool the solution is within the province of one of ordinary skill in the art informed by this disclosure.

The resulting crystals may be isolated by any method known to the art, such as by decanting the benzyl alcohol off the crystals or by filtration. Evaporation is also a suitable way to remove excess alcohol although heating of the crystals under high vacuum may be required to remove unsolvated benzyl alcohol by evaporation. Filtration is the preferred method of isolation. Residual solvent can be removed by vacuum filtration by allowing the isolated crystals to remain on the filter paper or sintered glass, whichever the case may be, for several minutes with heating and/or by rinsing with a volatile solvent in which benzyl alcohol is soluble but sertraline hydrochloride Form XI is not.

The novel Form XI of sertraline hydrochloride is useful as an intermediate in the preparation of sertraline hydrochloride Form X. By the methods of the present invention, sertraline hydrochloride Form XI is heated under vacuum for a sufficient amount of time to transform sertraline hydrochloride Form XI to sertraline hydrochloride Form X. The completeness of the transformation can be determined by sampling the material. Preferably, sertraline hydrochloride Form XI is heated to about 80° C., for about 24 h, which consistently results in the complete conversion to sertraline hydrochloride Form X. As described in more detail in commonly-assigned, co-pending U.S. application Ser. No. 09/448,985 filed Nov. 24, 1999, sertraline hydrochloride Form X is characterized by a powder X-ray diffraction pattern having principal peaks at 15.0±0.2, 16.0±0.2, 16.5±0.2, 17.0±0.2, 18.1±0.2, 21.0±0.2, 22.4±0.2, 24.9±0.2, 25.4±0.2, 26.2, 27.1, 28.4, and 29.0°±0.2 degrees two-theta. The IR spectrum of sertraline hydrochloride Form X is characterized by the following bands: 742, 776, 806, 824, 1002, 1017, 1028, 1060, 1079, 1135, 1218, 1314, 1336, and 1560 cm$^{-1}$. The DSC of sertraline hydrochloride Form X shows a small endotherm at about 190° C. followed by a melting endotherm at about 250° C.

The use of the novel sertraline hydrochloride Form XI of the present invention to prepare solutions of sertraline hydrochloride and benzyl alcohol in another solvent such as a syrup or elixir base or an ophthalmic solution or solution for injection is considered to be within the contemplated invention. Sertraline hydrochloride Form XI contains the antimicrobial agent benzyl alcohol. The use of sertraline hydrochloride Form XI in any solid state like a powder, granulate or compressed tablet, to prepare a solution containing sertraline hydrochloride and benzyl alcohol is taught by the present invention. The solid form can be dissolved in a solvent providing in one step sertraline hydrochloride as well as a preservative to increase the shelf life of the solution. Processing advantages flow from the use of sertraline hydrochloride Form XI for the preparation of a sertraline hydrochloride solution containing a preservative. Although not allowing much control of the proportion of benzyl alcohol to sertraline hydrochloride when sertraline hydrochloride Form XI is used alone, since the proportion is predetermined at 1:2 by the form itself, one skilled in the art will appreciate that the amount of alcohol can be reduced in relation to sertraline hydrochloride by using a mixture of sertraline hydrochloride Form XI and another form of sertraline hydrochloride, including, but not limited to sertraline hydrochloride sertraline hydrochloride Forms I–X, XII–XVI and amorphous sertraline hydrochloride, which do not contain benzyl alcohol. The advantages of adding the preservative and sertraline hydrochloride in the same step include simplifying the formulation process by omitting a separate addition step and potentially more accurately controlling the quantity of benzyl alcohol since a larger quantity of material is measured than when the preservative is added separately.

Sertraline Hydrochloride Form XII

Figure 3:
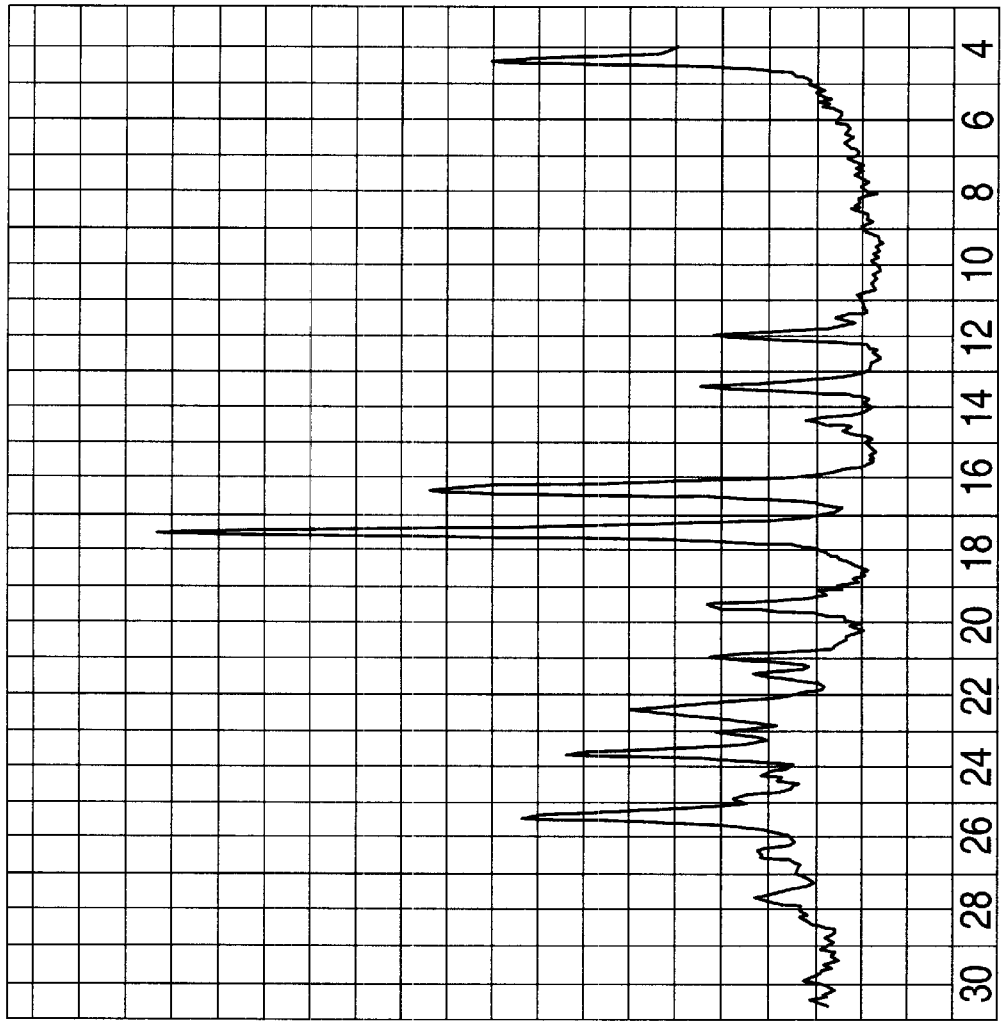
FIG. 3 is a characteristic powder X-ray diffraction pattern of sertraline hydrochloride Form XII.

Another embodiment of the present invention provides a new form of sertraline hydrochloride designated, sertraline hydrochloride Form XII, which is a hydrated form of sertraline hydrochloride, and processes for making sertraline hydrochloride Form XII. Sertraline hydrochloride Form XII may be obtained from any of the known forms of sertraline hydrochloride. Suitable forms of sertraline hydrochloride include, but are not limited to, sertraline hydrochloride Form I, Form II, Form III, Form V and anhydrous sertraline hydrochloride. Sertraline hydrochloride Form V is the preferred starting material. Sertraline hydrochloride Form XII can be made by exposing sertraline hydrochloride to water vapors. Sertraline hydrochloride Form V is exposed to water vapor for a time sufficient for the transformation to sertraline hydrochloride Form XII. Preferably, sertraline hydrochloride Form V is exposed to water vapor for about seven days. The transformation may be monitored by x-ray powder diffraction techniques. In order to preserve sertraline hydrochloride in an uncontaminated state when exposed to water vapor for a prolonged period of time, the starting sertraline hydrochloride should be placed in a sealed chamber. Sertraline hydrochloride Form XII is characterized by its powder X-ray diffraction pattern which has characteristic reflections at about 4.3±0.2, 12.0±0.2, 13.4±0.2, 14.4±0.2, 16.3±0.2, 17.4±0.2, 19.4±0.2, 20.9±0.2, 21.4±0.2, 22.4±0.2, 23.0±0.2, 23.5±0.2 and 25.3±0.2 degrees two-theta, as shown in FIG. 3. Of these, the reflections at about 4.3, 12.0, 13.4, 16.3 and 17.4±0.2 degrees are especially characteristic.

Sertraline Hydrochloride Form XIV

Another embodiment of the present invention provides sertraline hydrochloride Form XIV and processes for making sertraline hydrochloride Form XIV. Sertraline hydrochloride Form XIV may be obtained by dissolving sertraline hydrochloride in methanol and a non-polar solvent, such as hexane. Since, by the methods of the present invention, the starting material sertraline hydrochloride is completely dissolved, any form of sertraline hydrochloride may be used, including but not limited to, sertraline hydrochloride Forms I–X, XII–XVI and amorphous sertraline hydrochloride.

In one preferred method of making sertraline hydrochloride Form XIV, sertraline base is initially dissolved in a mixture of methanol and hexane. Preferred conditions involve addition of sertraline base to an approximately 1:1 mixture of methanol and hexane to produce an approximately 150–200 mM solution. Depending upon the concentration and ratio of methanol to the nonpolar solvent, heating may be required to facilitate the dissolution of sertraline base. After dissolution of the base is complete, gaseous hydrogen chloride is bubbled through the solution until a pH of about 0.5 to about 1.5, more preferably about 1.0 is attained. Sertraline hydrochloride Form XIV should precipitate from the solvent over time. If the gaseous hydrogen chloride is added at elevated temperature, then the solution may be allowed to cool, or be actively cooled, to a temperature below ambient, to induce crystallization. The precipitated sertraline hydrochloride Form XIV may be separated from the solvent conventionally, as by filtration or decanting.

In another embodiment of the present invention, sertraline hydrochloride Form XIV is made from sertraline hydrochloride Form II. By the method of the present invention, sertraline hydrochloride Form XIV is made by adding sertraline hydrochloride Form II to methanol to form a suspension. Preferably about 3 volumes of methanol are used, based on the weight of the sertraline hydrochloride Form II. However, lesser amounts of solvent will also effect the transformation, albeit in some instances more slowly. The transformation of sertraline hydrochloride Form II to sertraline hydrochloride Form XIV is accelerated by heating the suspension to an elevated temperature. The reflux temperature of methanol is suitable for accelerating the transformation sufficient that it is substantially complete in about an hour. The sertraline hydrochloride Form XIV may then be isolated conventionally, e.g., by decanting or filtering.

In another embodiment of the present invention, sertraline hydrochloride Form XIV is useful for preparing sertraline hydrochloride Form II. This process involves transforming sertraline hydrochloride Form XIV into Form II by suspending sertraline hydrochloride Form XIV in a solvent selected from the group consisting of ethyl acetate, acetone, and t-butyl-methyl-ether to form a suspension of sertraline hydrochloride. Typical loadings range from about 5 volumes to about 20 volumes of solvent based upon the weight of sertraline hydrochloride Form XIV, more preferably about 10 volumes (herein volumes based on weight is measured in units of milliliters/gram or equivalently liters/kilogram). The transformation of sertraline hydrochloride Form XIV to sertraline hydrochloride Form II is facilitated by heating the suspension to about 25° C. to the reflux temperature of the solvent. Preferably, the suspension is heated to reflux. The suspension is heated and stirred for a time sufficient for the transformation to sertraline hydrochloride Form II to be substantially complete. Preferably, the suspension is heated for about 2 to about 3 hours. The suspension is then cooled, or is allowed to cool, to further facilitate the transformation to sertraline hydrochloride Form II. Sertraline hydrochloride Form II is isolated conventionally, e.g., by decanting or filtering.

Figure 5:
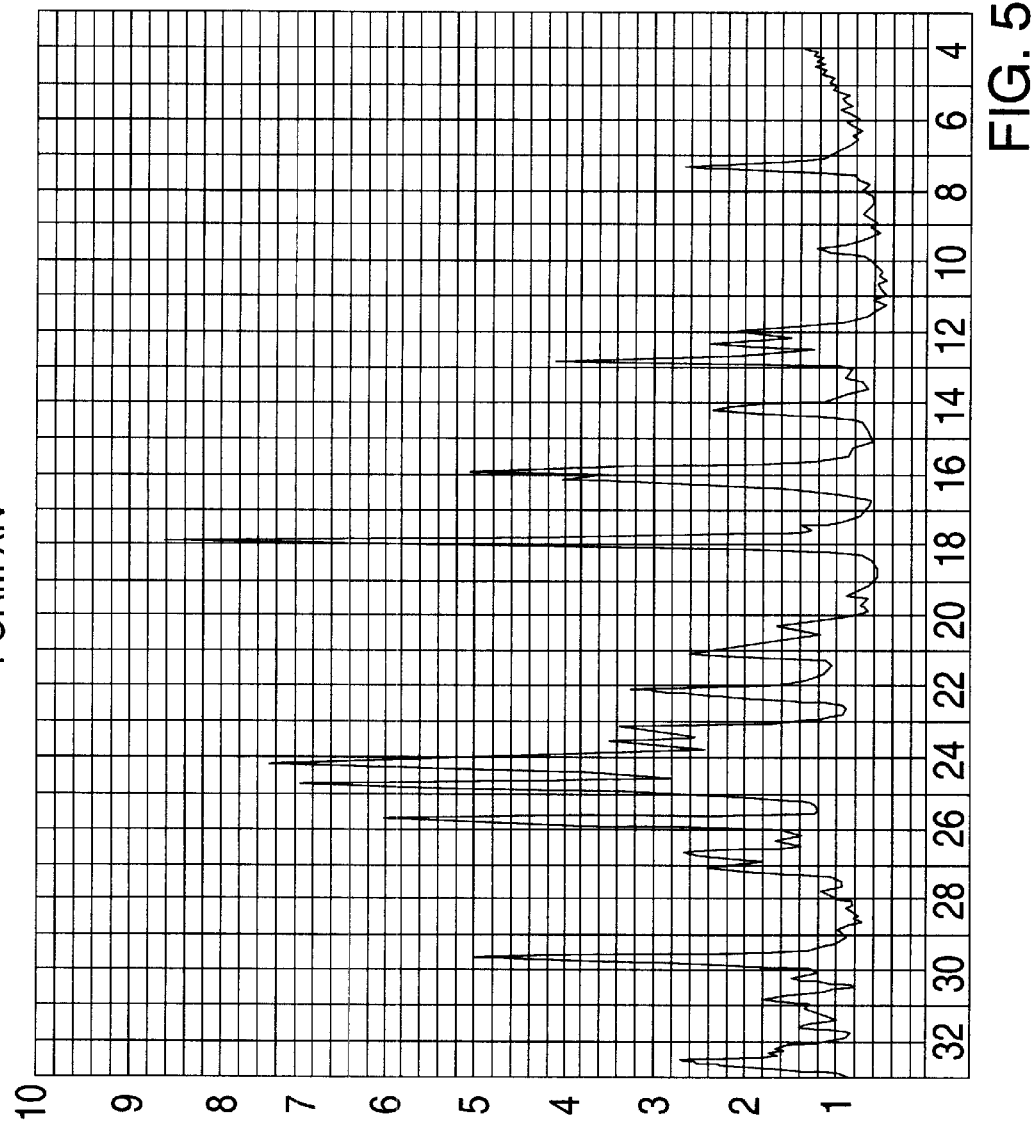
FIG. 5 is a characteristic powder X-ray diffraction pattern of sertraline hydrochloride Form XIV.

Sertraline hydrochloride Form XIV is characterized by a powder X-ray diffraction pattern having reflections at about 7.4±0.2, 9.6±0.2, 12.0±0.2, 12.8±0.2, 14.3±0.2, 16.0±0.2, 16.2±0.2, 18.0±0.2, 21.1±0.2, 23.2±0.2, 23.6±0.2, 24.3±0.2, 24.9±0.2, 25.7±0.2, 26.7±0.2, 29.6±0.2 and 32.5±0.2 degrees two-theta, as shown in FIG. 5.

Sertraline Hydrochloride Form XIII

Figure 4:
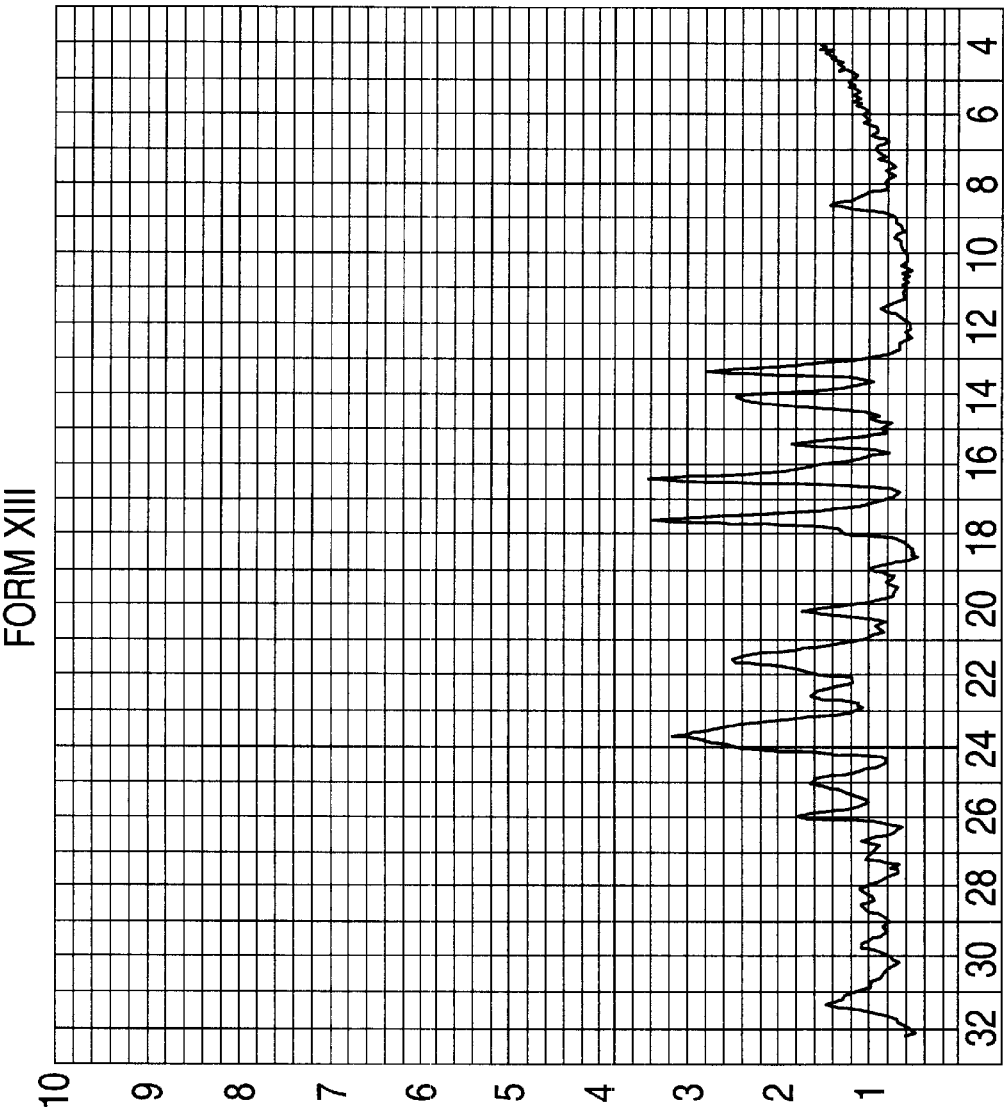
FIG. 4 is a characteristic powder X-ray diffraction pattern of sertraline hydrochloride Form XIII.

Another embodiment of the present invention provides a new form of sertraline hydrochloride designated sertraline hydrochloride Form XIII and processes for making sertraline hydrochloride Form XIII. By the methods of the present invention, sertraline hydrochloride Form XIII may be obtained by heating sertraline hydrochloride Form XIV crystals to a temperature of about 60° C. for about 24 hours. The sertraline hydrochloride Form XIII obtained in this manner is characterized by a powder X-ray diffraction pattern having reflections at about 8.5±0.2, 13.3±0.2, 14.0±0.2, 15.3±0.2, 16.3±0.2, 17.5±0.2, 20.1±0.2, 21.5±0.2, 22.5±0.2, 23.6±0.2, 25.0±0.2 and 25.9±0.2 degrees two-theta, as shown in FIG. 4.

Sertraline Hydrochloride Form XV

Another embodiment of the present invention provides a new form of sertraline hydrochloride designated sertraline hydrochloride Form XV and processes for making sertraline hydrochloride Form XV. By the methods of the present intention, sertraline hydrochloride Form XV may be obtained by precipitation from aqueous solutions of isopropanol with either sertraline base or sertraline hydrochloride as starting material.

In one preferred process for making sertraline hydrochloride Form XV, sertraline base initially is dissolved in isopropanol with a non-polar organic compound as co-solvent to facilitate dissolution of the sertraline base. A particularly preferred solvent is a mixture of isopropanol and hexane, more preferably an approximately 1:1 mixture of isopropanol:hexane. Under these preferred conditions, sertraline hydrochloride Form XV can be prepared without heating, though in solvent systems having a higher proportion of isopropanol or at higher sertraline base concentrations, heating may be required to obtain complete dissolution. Either concentrated or dilute aqueous hydrochloric acid is then added to deliver at least one equivalent of chloride per equivalent of sertraline base. The use of even highly concentrated aqueous hydrochloric acid provides sufficient water to favor the precipitation of sertraline hydrochloride in Form XV. The addition of the hydrogen chloride induces precipitation of sertraline as its hydrochloride salt over a period of hours without the need for active cooling below ambient temperature. However, if heating was used to dissolve the sertraline base then cooling of the solution to ambient temperature may further induce crystallization. The precipitated crystals may then be isolated conventionally, e.g., by filtering or decanting, to yield sertraline hydrochloride Form XV.

In another embodiment of the present invention, sertraline hydrochloride Form XV is made by the process of adding sertraline base to isopropanol to form a suspension. Preferably, the isopropanol is warmed to about 40–50° C. either before or after addition of the sertraline base. Aqueous hydrochloric acid is then added to the mixture of sertraline base and isopropanol in an amount sufficient to form sertraline hydrochloride. The resulting suspension of sertraline hydrochloride is heated to facilitate dissolution of sertraline hydrochloride. Preferably the reaction is heated to about 60° C. Water is also added during heating of the sertraline hydrochloride solution to facilitate complete dissolution. Upon complete dissolution, the mixture is stirred at room temperature for a time sufficient to induce the transformation to sertraline hydrochloride Form XV and precipitation of sertraline hydrochloride Form XV. The precipitated sertraline hydrochloride Form XV may then be isolated by conventional methods.

Sertraline base for use in the processes of the present invention may be produced by dissolving sertraline mandelate in ethyl acetate followed by neutralization of the sertraline mandelate with aqueous sodium hydroxide. The organic phase is separated from the aqueous phase and dried using magnesium sulfate. The solvent is removed under reduced pressure to produce sertraline base as an oil. Methods for making sertraline base are set forth in U.S. Pat. Nos. 4,536,518 and 5,248,699, the contents of which are incorporated herein by reference.

In another embodiment of the present invention, sertraline hydrochloride Form XV is made from sertraline hydrochloride Form VI. Co-pending U.S. application Ser. No. 09/448,985 discloses sertraline hydrochloride Form VI and processes for making sertraline hydrochloride Form VI. Sertraline hydrochloride Form VI may be made according to the following Examples 18, 19, and 20 and is characterized by a powder x-ray diffraction pattern comprising peaks at 7.3±0.2, 12.1±0.2, 12.7±0.2, 14.0±0.2, 15.6 ±0.2, 17.6±0.2, 20.1±0.2, 20.6±0.2, 21.9±0.2, 22.7±0.2, 23.0±0.2, 23.8±0.2, 24.3±0.2, 25.4±0.2, and 26.3±0.2 degrees two-theta.

By the methods of the present invention, sertraline hydrochloride Form XV may be prepared by suspending sertraline hydrochloride Form VI in aqueous isopropanol. Preferably, about 1 to about 4, more preferably about 3 volumes, of isopropanol is used based on the weight of the sertraline hydrochloride starting material. Sertraline hydrochloride Form XV is preferably prepared by recrystallization from such a suspension using a solvent system comprising isopropanol and water in a ratio of about 5:1 to about 7:1 (v/v), and more preferably about 6:1. Water may be provided by using aqueous isopropanol or by adding water to either anhydrous isopropanol or aqueous isopropanol in order to bring the water content within the afore-mentioned preferred range. The suspension is stirred for a time sufficient to facilitate the transformation of sertraline hydrochloride Form VI to sertraline hydrochloride Form XV. The transformation may be monitored by x-ray diffraction methods. The suspension is preferably heated to accelerate the transformation of sertraline hydrochloride Form VI to sertraline hydrochloride Form XV, the reflux temperature of isopropanol being a suitable temperature for this purpose. Sertraline hydrochloride Form XV may be isolated conventionally, e.g., by decanting or filtering, with optional washing of the crystals with isopropanol.

Figure 6:
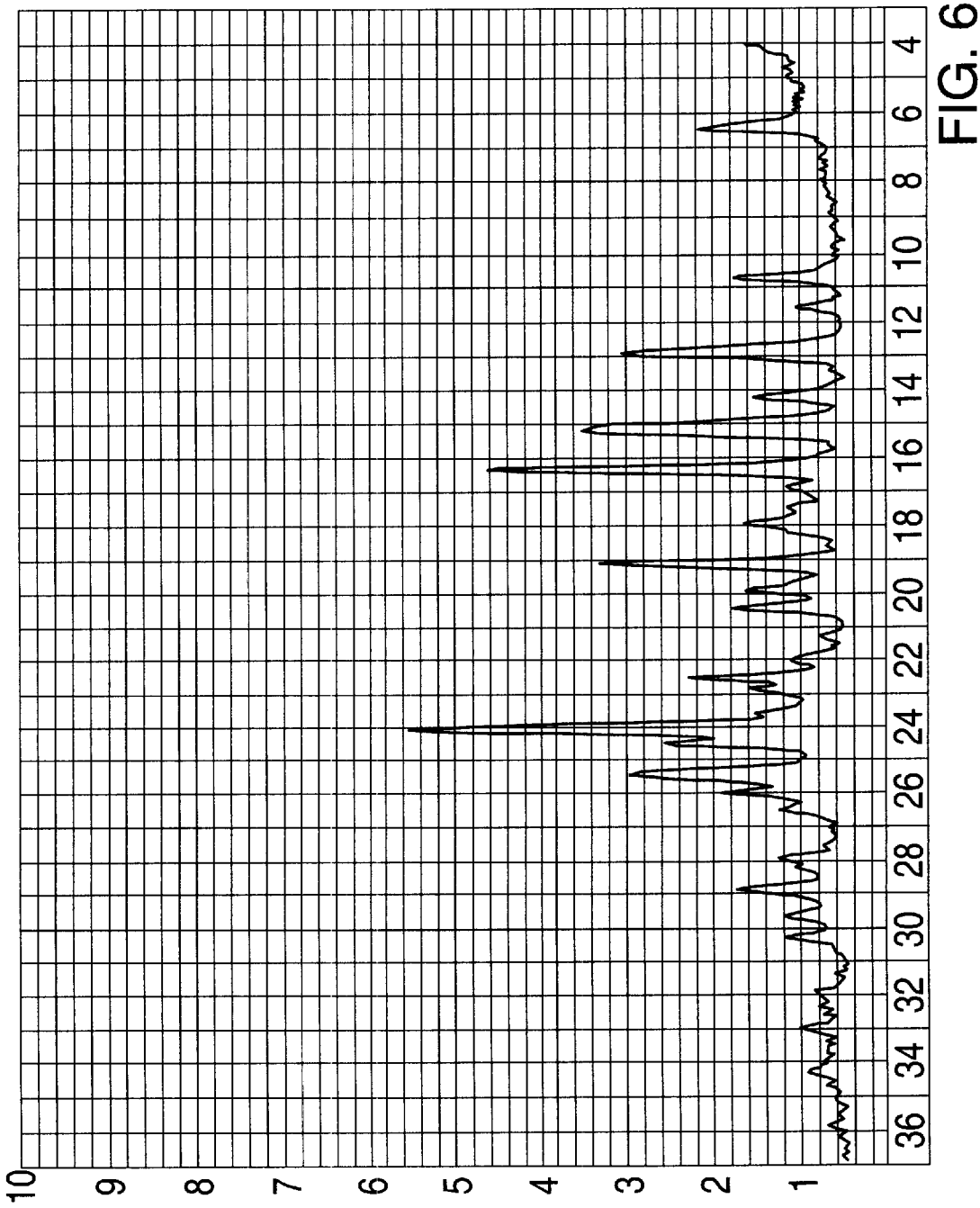
FIG. 6 is a characteristic powder X-ray diffraction pattern of sertraline hydrochloride Form XV.

Sertraline hydrochloride Form XV is characterized by a powder X-ray diffraction pattern having reflections at about 6.5±0.2, 10.7±0.2, 12.9±0.2, 14.2±0.2, 15.2±0.2, 16.6±0.2, 17.5±0.2, 18.1±0.2, 19.9±0.2, 20.4±0.2 24.0±0.2 and 24.5±0.2 degree theta, as shown in FIG. 6.

In another embodiment of the present invention, sertraline hydrochloride Form V can be prepared from sertraline hydrochloride Forms XIV and XV. Each of these novel forms can be transformed to sertraline hydrochloride Form V by heating crystals of the novel forms, preferably to 70° C. or above, more preferably 80° C. or above, for sufficient time to complete the transformation. The reaction may be monitored by powder x-ray diffraction methods. The transformation to sertraline hydrochloride Form V is substantially complete after heating sertraline hydrochloride Forms XIV or XV to 80° C. for 24 hours.

In another embodiment of the present invention, sertraline hydrochloride Form XV is useful for preparing sertraline hydrochloride Form II. This process involves transforming sertraline hydrochloride Form XV into sertraline hydrochloride Form II by suspending sertraline hydrochloride Form XV in a solvent selected from the group consisting of ethyl acetate, acetone, t-butyl-methyl-ether (MTBE) and cyclohexane. Typical loadings range from about 5 volumes to about 20 volumes of solvent based upon the weight of sertraline hydrochloride Form XV, more preferably about 10 volumes (herein volumes based on weight is measured in units of milliliters/gram or equivalently liters/kilogram). The transformation of sertraline hydrochloride Form XV to sertraline hydrochloride Form II is facilitated by heating the suspension to about 25° C. to the reflux temperature of the solvent. Preferably, the suspension is heated to reflux. The suspension is refluxed for a time sufficient for the transformation to sertraline hydrochloride Form II to be substantially complete. Preferably, the suspension is heated for about 2 to about 3 hours. Alternatively, the suspension may be stirred at room temperature for a time sufficient to facilitate the transformation of sertraline hydrochloride Form XV to sertraline hydrochloride Form II. Completion of the transformation may be determined by monitoring the reaction using a suitable means, e.g., x-ray powder diffraction methods. Upon conversion of sertraline hydrochloride Form XV to sertraline hydrochloride Form II, the suspension is then cooled to a temperature range of about room temperature to about 5° C. to further facilitate the transformation to sertraline hydrochloride Form II. The sertraline hydrochloride Form II is isolated conventionally, e.g., by decanting or filtering.

Sertraline Hydrochloride Form XVI

Figure 7:
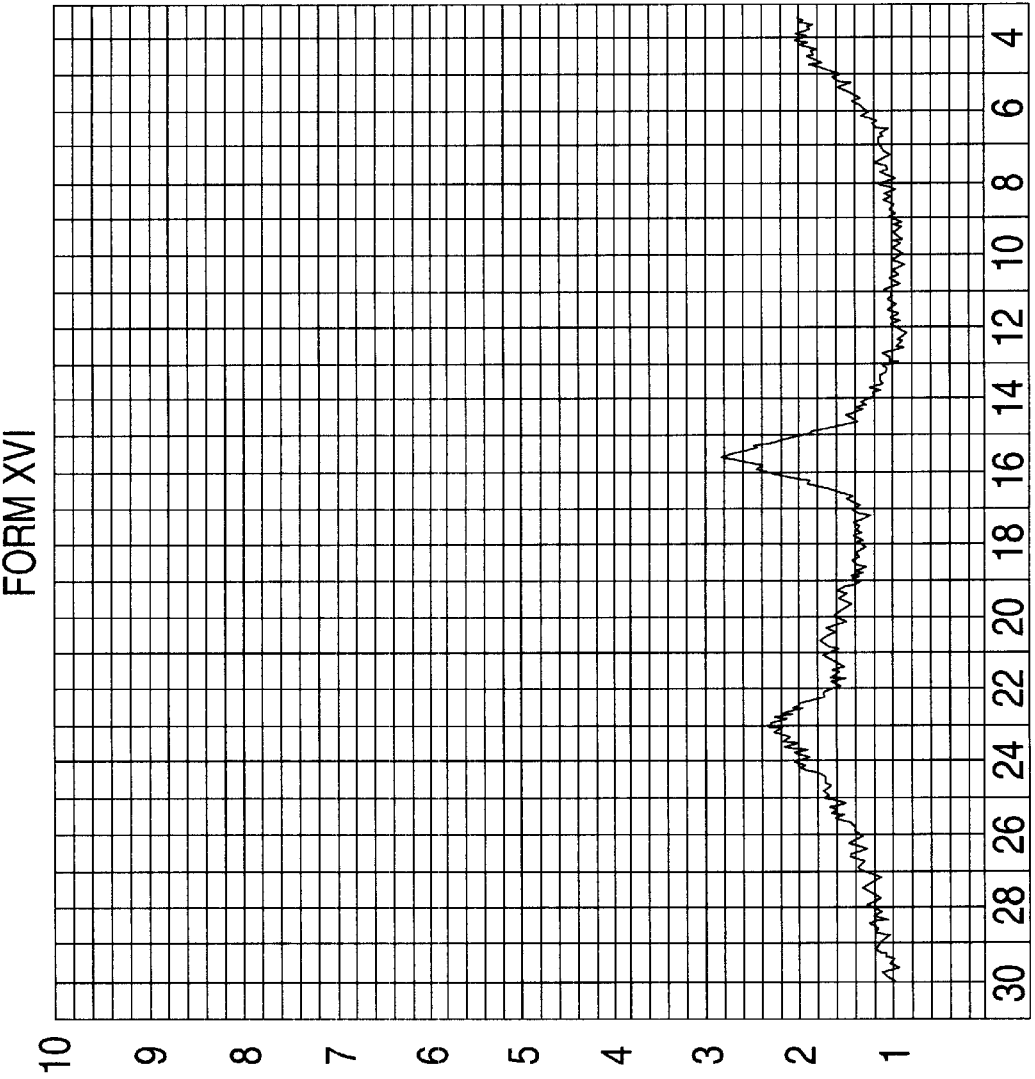
FIG. 7 is a characteristic powder X-ray diffraction pattern of sertraline hydrochloride Form XVI.

The novel form of sertraline hydrochloride designated Form XVI and processes for preparing sertraline hydrochloride Form XVI have also been discovered. Sertraline hydrochloride Form XVI is a form of sertraline hydrochloride with low-crystallinity which can be distinguished from truly amorphous sertraline hydrochloride by the presence of broad peaks at about 15.6 and 23.0±0.2 degrees two-theta, as shown in FIG. 7, and can be distinguished from other more crystalline forms by absence of the characteristic reflections of those forms. Sertraline hydrochloride Form XVI may be prepared from sertraline base by precipitation from a solution in a single component, non-aqueous, nonpolar solvent system selected from the group consisting of hexane, cyclohexane and toluene.

According to the preferred process for obtaining sertraline hydrochloride Form XVI, sertraline base is initially dissolved in hexane, cyclohexane or toluene. About 5 to about 20 volumes of solvent, more preferably about 10 volumes, are used per weight of sertraline base. At this loading, it may be necessary to heat the suspension to an elevated temperature to facilitate the dissolution of the sertraline base in the solvent, in which case the preferred elevated temperature is from about 30° C. to the reflux temperature of the solvent, more preferably from about 40° C. to the reflux temperature of the solvent. Although the formation of a clear solution is preferable, it is not strictly required since any undissolved sertraline base will go into solution as sertraline hydrochloride Form XVI precipitates as will become apparent from the following description.

Gaseous hydrogen chloride is bubbled through the solution (or suspension) containing sertraline base until a pH of about 1 to about 1.5 is reached. Addition of the hydrogen chloride induces precipitation of the sertraline hydrochloride salt. Precipitation of the salt reduces the concentration of the sertraline base in solution which allows the dissolution of more of the sertraline base if any remains undissolved. Monitoring of the pH of the solution and maintenance additions of hydrogen chloride, if necessary, are recommended in such a case to maintain the pH of the solution in the preferred range. At some of the loadings recommended for practice of this method, gel formation may occur. Any gel that forms typically may be broken up so as to allow filtration or decanting, by continued stirring of the mixture. After precipitation is substantially complete the crystals may be isolated conventionally by filtering or decanting, optionally washing with solvent, to yield sertraline hydrochloride Form XVI.

In another embodiment of the present invention, sertraline hydrochloride Form XVI is useful for preparing sertraline hydrochloride Form II. This process involves transforming sertraline hydrochloride Form XVI into sertraline hydrochloride Form II by suspending Form XVI in a solvent selected from ethyl acetate and acetone. Typical loadings range from about 5 volumes to about 20 volumes of solvent based upon the weight of sertraline hydrochloride, more preferably about 10 volumes (herein volumes based on weight is measured in units of milliliters/gram or equivalently liters/kilogram). Sertraline hydrochloride Form XVI is suspended for a time sufficient to induce the transformation of sertraline hydrochloride Form XVI to sertraline hydrochloride Form II. The suspension may be stirred. The transformation of sertraline hydrochloride Form XVI into sertraline hydrochloride Form II is facilitated by heating, the reflux temperature of the solvents being suitable for facilitated the transformation to sertraline hydrochloride Form II sufficient that the transformation is substantially complete in about two hours. The suspension of sertraline hydrochloride Form II is then cooled or is allowed to cool, preferably to room temperature. Sertraline hydrochloride Form II is isolated conventionally, e.g., by decanting or filtering.

Pharmaceutical Compositions Containing Sertraline Hydrochloride Polymorphs

In accordance with the present invention, the novel sertraline hydrochloride Forms XI–XVI may be prepared as pharmaceutical compositions which are particularly useful for treatment of depression, obsessive-compulsive disorder and panic disorder. As illustrated by the above-described use of sertraline hydrochloride Form XI with other forms to prepare syrups, elixirs and solutions, compositions of the present invention generally may contain the novel forms of the present invention alone or in mixture with other forms of sertraline hydrochloride. Such compositions may also contain a pharmaceutically acceptable vehicle, i.e. one or more pharmaceutical excipients. Whether administered in pure form, mixed together or in a composition containing pharmaceutical excipients, the form(s) may be in powder, granule, aggregate or any other solid state.

For example, these compositions may be prepared as medicaments to be administered orally, parenterally, rectally, transdermally, bucally or nasally. Suitable forms for oral administration include tablets, compressed or coated pills, dragees, sachets, hard or gelatin capsules, sub-lingual tablets, syrups, elixirs and suspensions. Suitable forms for parenteral administration include an aqueous or non-aqueous solution or emulsion, while for rectal administration, suitable forms for administration include suppositories with hydrophilic or hydrophobic vehicle. For topical administration, the invention provides suitable transdermal delivery systems known in the art, and for nasal delivery there are provided suitable aerosol delivery systems known in the art.

Compositions for making tablets may have few or many components depending upon the tableting method used, the release rate desired and other factors. For example, compositions of the present invention may contain diluents such as cellulose-derived materials such as powdered cellulose, microcrystalline cellulose, microfine cellulose, methyl cellulose, ethyl cellulose, hydroxyethyl cellulose, hydroxypropyl cellulose, hydroxypropylmethyl cellulose, carboxymethyl cellulose salts and other substituted and unsubstituted celluloses; starch; pregelatinized starch; inorganic diluents like calcium carbonate and dibasic calcium diphosphate and other diluents known to the pharmaceutical industry. Other suitable diluents include waxes, sugars and sugar alcohols such as mannitol and sorbitol, acrylate polymers and copolymers, as well as pectin, dextrin and gelatin.

Other excipients include binders, such as acacia gum, pregelatinized starch, sodium alginate, glucose and other binders used in wet and dry granulation and direct compression tableting processes. Excipients that may also be present in a solid composition of the novel forms of sertraline hydrochloride further include disintegrants such as sodium starch glycolate, crospovidone, low-substituted hydroxypropyl cellulose and others. Additional excipients include tableting lubricants such as magnesium and calcium stearate, sodium stearyl fumarate and polyethylene glycol; flavorings; sweeteners; preservatives; pharmaceutically acceptable dyes and glidants such as silicon dioxide.

Capsule dosages, of course, will contain the composition within a capsule which may be made of gelatin or other encapsulating material. Tablets and powders may be coated. The coating may be an enteric coating or non-enteric coating. Suitable coatings for enteric-coated powder forms include phthalic acid cellulose acetate, hydroxypropylmethyl cellulose phthalate, polyvinyl alcohol phthalate, carboxymethylethylcellulose, a copolymer of styrene and maleic acid, a copolymer of methacrylic acid and methyl methacrylate, and like materials, and if desired, they may be employed with suitable plasticizers and/or extending agents. A coated tablet may have a coating on the surface of the tablet or may be a tablet comprising a powder or granules with an enteric-coating.

The preferred dosage of the present invention is an oral tablet. Other oral dosage forms including pills, capsules, dragees, cachets, troches, pellets, suspensions, powders, lozenges, elixirs and the like may also be used, as well as suppositories, ointments, suspensions and parenteral and ophthalmic suspensions. In addition, the forms of the present invention may be dissolved in solutions to deliver sertraline hydrochloride and a solvate.

Preferred solid oral dosages of the present invention contain from about 25 mg to about 200 mg of sertraline hydrochloride Forms XI, XII, XIII, XIV, XV, XVI or their mixtures. More preferable oral dosages contain about 50–120 mg of one or more of the novel sertraline hydrochloride forms.

The powder X-ray diffraction patterns were obtained by methods known in the art using a Philips X-ray powder diffractometer, goniometer model 1050/70, at a scanning speed of 2° min.$^{-1}$ with Cu radiation of $\lambda$=1.5418 Å.

The infrared spectra were obtained by methods known in the art using a Perkin Elmer FT-IR Paragon 1000 spectrometer. Samples were analyzed in Nujol mulls. Spectra were obtained at 4 cm$^{-1}$ resolution and 16 scans each.

Having thus described the present invention with reference to certain preferred embodiments, the following examples are provided to further illustrate methods by which novel forms of sertraline hydrochloride may be obtained. One skilled in the art will recognize variations and substitutions in the methods as described and exemplified which do not depart from the spirit and scope of the invention.

EXAMPLES

Example 1

Preparation of Sertraline Hydrochloride Form XI

Sertraline hydrochloride (10 g) was added to benzyl alcohol (30 mL) in a three necked round bottom flask equipped with a condenser, thermometer and mechanical stirrer. The resulting suspension was stirred as it was slowly heated to 100° C. After the mixture had clarified, the resulting solution was slowly cooled from 100° C. to 25° C. over a period of two hours. Crystals formed and were isolated by filtration. The crystals were rinsed with fresh benzyl alcohol and analyzed without further purification or drying. The crystals were identified as sertraline hydrochloride Form XI by their powder X-ray spectrum.

Thermogravimetric analysis showed that the sample lost 12–14% of its weight on heating to 150° C. corresponding to complete loss of benzyl alcohol from a benzyl alcohol hemi-solvate of sertraline hydrochloride.

Example 2

Preparation of Sertraline Hydrochloride Form X from Form XI

Sertraline hydrochloride Form XI was heated to 80° C. under vacuum for 24 h. The resulting material was then cooled under vacuum to ambient temperature. The resulting material was found to be sertraline hydrochloride Form X.

Example 3

Preparation of Sertraline Hydrochloride Form XII

Sertraline hydrochloride Form V (100 mg) was placed in a 10 mL glass bottle. The uncapped bottle was set in a pool of water at the bottom of a larger bottle. The large bottle was sealed and the sertraline hydrochloride Form V crystals were kept in the moist environment for one week. The crystals of sertraline hydrochloride Form XII that were recovered at the end of the week were characterized by their powder X-ray diffraction pattern that exhibited reflections at 4.3, 12.0, 13.4, 14.4, 16.3, 17.4, 19.4, 20.9, 21.4, 22.4, 23.0, 23.5 and 25.3 (±0.2) degrees 2 θ.

Example 4

Preparation of Sertraline Hydrochloride Form XIV

Sertraline base (10 g) was dissolved in a mixture of methanol (100 mL) and hexane (100 mL). Gaseous HCl was bubbled through the mixture at 35° C. until a pH of 1 was reached, at which point the mixture had clarified. The resulting solution was stirred at 30° C. for two hours over which time crystals formed. The crystals were filtered and were identified as sertraline hydrochloride Form XIV by their powder X-ray spectrum that exhibited reflections at 7.4±0.2, 9.6±0.2, 12.0±0.2, 12.8±0.2, 14.3±0.2, 16.0±0.2, 16.2±0.2, 18.0±0.2, 21.1±0.2, 23.2±0.2, 23.6±0.2, 24.3±0.2, 24.9±0.2, 25.7±0.2, 26.7±0.2, 29.6±0.2 and 32.5±0.2 degrees two-theta.

Example 5

Preparation of Sertraline Hydrochloride Form XIII from Form XIV

Sertraline hydrochloride Form XIV crystals were dried at 60° C. for 24 hours. The dried crystals were identified as sertraline hydrochloride Form XIII by their powder X-ray spectrum.

Example 6

Preparation of Sertraline Hydrochloride Forms XIV from Form II

Sertraline hydrochloride Form II (7 g) was suspended in methanol (21 mL) and was heated to reflux for 1 h. The solution was allowed to cool to room temperature, whereupon crystals formed in the solution. The crystals were isolated by filtration and were identified as sertraline hydrochloride Form XIV by their powder X-ray diffraction pattern.

Example 7

Preparation of Sertraline Hydrochloride form V from Form XIV

Sertraline hydrochloride Form XIV crystals were dried at 80° C. for 24 h to give sertraline hydrochloride Form V.

Example 8

Preparation of Sertraline Hydrochloride Form XV from Sertraline Base

Sertraline base (10 g) was dissolved in a 1:1 (v:v) mixture of isopropanol:hexane (200 mL) at room temperature. Hydrochloric acid was then stirred into the solution to facilitate the precipitation of sertraline hydrochloride Form XV. The solution was stirred at room temperature while crystals formed in the solution. The crystals were isolated by filtration and washed with the 1:1 isopropanol:hexane (2×10 mL). The crystals were identified as a novel form of sertraline hydrochloride (designated sertraline hydrochloride Form XV) by powder X-ray spectroscopy.

Example 9

Preparation of Sertraline Hydrochloride Form XV from Sertraline Base

Sertraline base (26.5 g) was added to isopropanol (85 ml) at 45° C. Hydrochloric acid (8 mL) was then stirred into the warm solution. The resulting suspension was heated to about 60° C. and water was added to facilitate complete dissolution of sertraline hydrochloride. The solution was then cooled to room temperature and stirred for 2.5 hrs to facilitate the formation of and precipitation of sertraline hydrochloride Form XV. Sertraline hydrochloride Form XV was isolated by conventional methods, including, but not limited to, filtration.

Example 10

Preparation of Sertraline Hydrochloride Form XV from Form VI

Sertraline hydrochloride Form VI (40 g) was suspended in isopropanol (120 mL) and heated to reflux temperature. The sertraline hydrochloride remained undissolved. Water (20 mL) was slowly added to the warm suspension until the sertraline hydrochloride dissolved. The solution was then allowed to cool. After cooling to about 40° C., the mixture started to gel. The gel was redissolved by addition of isopropanol and reheating to reflux temperature for a few minutes. The solution was then allowed to cool again to room temperature and was stirred at room temperature for 1 h, over which time crystals formed in the solution. Sertraline hydrochloride Form XV crystals were isolated by filtration and washed with isopropanol (2×20 mL).

Example 11

Preparation of Sertraline Hydrochloride Form V from Form XV

The Form XV crystals were then dried at 80° C. for 24 h to produce sertraline hydrochloride Form V.

Example 12

Preparation of Sertraline Hydrochloride Form XVI from Sertraline Base

Sertraline base (5 g) was suspended in cyclohexane (50 mL) and the suspension was heated to about 60° C. to dissolve the sertraline base. Gaseous hydrochloric acid was bubbled into the solution until a pH of about 1–1.5 was reached. Bubbling was ceased and the solution was allowed to cool to about 40° C., whereupon crystals formed in the solution. Cyclohexane was removed by filtration and the residue was identified as a new form of sertraline hydrochloride, designated Form XVI, by powder X-ray spectroscopy. The powder X-ray spectrum of Form XVI has two broad reflections at 15.6 and 23.0 at 2 θ.

Example 13

Preparation of Sertraline Hydrochloride Form V from form XVI

Sertraline Hydrochloride Form XVI crystals were heated to 80° C. for 24 h to give sertraline hydrochloride Form V.

Example 14

Preparation of Sertraline Hydrochloride Form XVI from Sertraline Base

Sertraline base (5 g) was suspended in hexane (50 mL) and the suspension was heated to 40° C. to dissolve the base. The solution was then allowed to cool to 30° C. and gaseous hydrochloric acid was bubbled into the solution until the pH of the solution reached about 1.5. The solution gelled while it was being acidified but remained stirrable. The gel was stirred at room temperature for 2 hours. Sertraline hydrochloride Form XVI precipitated from the hexane. The hexane was removed by filtration and the residue was washed with fresh hexane. The residue was determined to be sertraline hydrochloride Form XVI.

Example 15

Preparation of Sertraline Hydrochloride Form XVI from Sertraline Base

Sertraline base (5.8 g) was dissolved in toluene (200 mL). Gaseous hydrochloric acid was bubbled ( about pH 1.5) through the solution to induce the formation of sertraline hydrochloride Form XVI. The solution gelled while it was being acidified but remained stirrable. Filtration and drying at 50° C. for 16 hours yields sertraline hydrochloride Form XVI (6.61 gr.).

Example 16

Preparation of Sertraline Hydrochloride Form II from Form XVI

Sertraline hydrochloride Form XVI (5 g) was suspended in ethyl acetate (50 mL) and the suspension was refluxed for 2 h. The suspension was then cooled to about 40° C. and filtered. The solid residue was found to be sertraline hydrochloride Form II.

Example 17

Preparation of Sertraline Hydrochloride Form II from Form XVI

Sertraline hydrochloride Form XVI (5 g) was suspended in acetone (50 mL) and the suspension was refluxed for 2 h. The suspension was then cooled to about 40° C. and filtered. The solid residue was found to be sertraline hydrochloride Form II.

Example 18

Preparation of Sertraline Hydrochloride Ethanolate Form VI by Reslurry of Form I Sertraline hydrochloride Form I (1 g) and absolute ethanol (20 mL) were stirred at room temperature for 24 hours. Filtration of the mixture yielded sertraline hydrochloride ethanolate-Form VI.

Example 19

Preparation of Sertraline Hydrochloride Ethanolate Form VI-by Reslurry of Form II Sertraline hydrochloride Form II (1 g) and absolute ethanol (20 mL) were stirred at room temperature for 24 hours. Filtration of the mixture yielded sertraline hydrochloride ethanolate Form VI.

Example 20

Preparation of Sertraline Hydrochloride Ethanolate—Form VI—from Form V

Sertraline hydrochloride Form V (1 g) and ethanol absolute (20 mL.) were stirred at room temperature for 24 hrs. Filtration of the mixture yielded sertraline hydrochloride ethanolate Form VI.

Example 21

Preparation of Sertraline Hydrochloride Form II from Form XIV

Sertraline hydrochloride Form XIV (3 g) was suspended in ethyl acetate (45 mL). The suspension was heated at reflux for 2 hours to facilitate the transformation of sertraline hydrochloride Form XIV to sertraline hydrochloride Form II. The suspension was then cooled. Sertraline hydrochloride Form II was isolated by filtration.

Example 22

Preparation of Sertraline Hydrochloride Form II from Form XIV

Sertraline hydrochloride Form XIV (3 g) was suspended in acetone (30 ml). The suspension was heated at reflux for 2 hours to facililtate the transformation of sertraline hydrochloride Forn XIV to sertraline hydrochloride Form II. The suspension was then cooled. Sertraline hydrochloride Form II was isolated by filtration.

Example 23

Preparation of Sertraline Hydrochloride Form II from Form XIV

Sertraline hydrochloride Form XIV (3 g) was suspended in t-butyl-methyl-(MTBE). The suspension was heated at reflux for 3 hours to facilitate the transformation of sertraline hydrochloride Form XIV to sertraline hydrochloride Form II. The suspension was then cooled. Sertraline hydrochloride Form II was isolated by filtration.

Example 24

Preparation of Sertraline Hydrochloride Form II from Form XV

Sertraline hydrochloride Form XV (23 g) with LOD (loss on drying) 30% was suspended in ethyl acetate (230 mL) preheated at 40° C. The suspension was heated at reflux for 2 hours to facilitate the transformation of sertraline hydrochloride Form XV to sertraline hydrochloride Form II. The suspension was then cooled. Sertraline hydrochloride Form II was isolated by filtration.

Example 25

Preparation of Sertraline Hydrochloride Form II from Form XV

Sertraline hydrochloride Form XV (6 g) was suspended in acetone (60 ml). The suspension was heated at reflux for 3 hours to facilitate the transformation of sertraline hydrochloride Form XV to sertraline hydrochloride Form II. The suspension was then cooled. Sertraline hydrochloride Form II was isolated by filtration.

Example 26

Preparation of Sertraline Hydrochloride Form II from Form XV

Sertraline hydrochloride Form XV (30 g) with LOD 54% was suspended in t-butyl-methyl-(MTBE) (300 ml) preheated at 40° C. The suspension was heated at reflux for 3 hours to facilitate the transformation of sertraline hydrochloride Form XV to sertraline hydrochloride Form II. The suspension was then cooled. Sertraline hydrochloride Form II was isolated by filtration.

Example 27

Preparation of Sertraline Hydrochloride Form II from Form XV

Sertraline hydrochloride Form XV (6 g) was suspended in cyclohexane (60 ml). The suspension was heated at 60° C. for 3 hours to facililtate the transformation of sertraline hydrochloride Form XV to sertraline hydrochloride Form II. The suspension was then cooled. Sertraline hydrochloride Form II was isolated by filtration.

It should be understood that some modification, alteration and substitution is anticipated and expected from those skilled in the art without departing from the teachings of the invention. Accordingly, it is appropriate that the following claims be construed broadly and in a manner consistent with the scope and spirit of the invention.

We claim:

1. Sertraline hydrochloride Form XI.
2. Sertraline hydrochloride Form XI which is characterized by a powder X-ray diffraction pattern comprising peaks at about 16.0±0.2, 17.7±0.2, 20.7±0.2, 24.9±0.2 and 29.2±0.2 degrees two-theta.
3. The sertraline hydrochloride Form XI of claim 2 which is characterized by a powder X-ray diffraction pattern comprising peaks at about 6.9±0.2, 8.7±0.2, 9.7±0.2, 14.0±0.2, 16.0±0.2, 17.3±0.2, 17.7±0.2, 20.3±0.2, 20.7±0.2, 22.1±0.2, 22.5±0.2, 23.0±0.2, 23.8±0.2, 24.9±0.2, and 29.2±0.2 degrees two-theta.
4. Sertraline hydrochloride Form XI which is characterized by an infrared absorption comprising bands at 739, 1040, 1201, 1560 and 1595 cm$^{-1}$.
5. The sertraline hydrochloride Form XI of claim 4 which is characterized by an infrared absorption comprising bands at 698, 739, 750, 781, 817, 838, 886, 954, 1001, 1030, 1040, 1075, 1134, 1201, 1312, 1328, 1493, 1560, and 1595 cm$^{-1}$.
6. A process for making sertraline hydrochloride Form XI comprising the steps of:
    (a) dissolving sertraline hydrochloride in benzyl alcohol to form a sertraline hydrochloride solution;
    (b) crystalizing sertraline hydrochloride Form XI from the sertraline hydrochloride solution; and
    (c) isolating the sertraline hydrochloride Form XI.
7. The process of claim 6 wherein the sertraline hydrochloride Form XI is sertraline hydrochloride benzyl alcohol hemi-solvate.
8. The process of claim 6 wherein the sertraline hydrochloride Form XI is a mono-solvate, di-solvate or tri-solvate.
9. The process of claim 6 wherein the sertraline hydrochloride Form XI is benzyl alcohol solvate.
10. The process of claim 6 further comprising the step of heating the solution to facilitate dissolution.
11. A process of making sertraline hydrochloride Form X comprising the step of heating sertraline hydrochloride Form XI.
12. The process of making sertraline hydrochloride Form X of claim 11 wherein sertraline hydrochloride Form XI is heated under vacuum.
13. Sertraline hydrochloride Form XII.
14. Sertraline hydrochloride Form XII hydrate.
15. Sertraline hydrochloride Form XII mono-hydrate.
16. Sertraline hydrochloride Form XII which is characterized by a powder X-ray diffraction pattern comprising peaks at about 4.3±0.2, 12.0±0.2, 13.4±0.2, 16.3±0.2, and 17.4±0.2 degrees two-theta.
17. The sertraline hydrochloride Form XII of claim 16 which is characterized by a powder X-ray diffraction pattern comprising peaks at about 4.3±0.2, 12.0±0.2, 13.4±0.2, 14.4±0.2, 16.3±0.2, 17.4±0.2, 19.4±0.2, 20.9±0.2, 21.4±0.2, 22.4±0.2, 23.0±0.2, 23.5±0.2 and 25.3±0.2 degrees two-theta.
18. A process for making sertraline hydrochloride Form XII comprising the steps of:
    (a) exposing sertraline hydrochloride to water vapor; and
    (b) isolating sertraline hydrochloride Form XII.
19. The process of claim 18 wherein the sertraline hydrochloride of step (a) is setraline hydrochloride Form V.
20. Sertraline hydrochloride Form XIV.
21. Sertraline hydrochloride Form XIV which is characterized by a powder x-ray diffraction pattern comprising peaks at about 7.4±0.2, 9.6±0.2, 12.0±0.2, 12.8±0.2, 14.3±0.2, 16.0±0.2, 16.2±0.2, 18.0±0.2, 21.1±0.2, 23.2±0.2, 23.6±0.2, 24.3±0.2, 24.9±0.2, 25.7±0.2, 26.7±0.2, 29.6±0.2 and 32.5±0.2 degrees two-theta.
22. A process for making sertraline hydrochloride Form XIV comprising the steps of:
    (a) dissolving sertraline base in a solvent mixture of methanol and hexane to form a solution of sertraline base and the solvent;
    (b) adding hydrogen chloride to the solution to attain a pH of from about 0.5 to about 1.5;
    (c) precipitating sertraline hydrochloride from the solution;
    (d) removing the solvent; and
    (e) isolating sertraline hydrochloride Form XIV.
23. The process of claim 22 wherein the solvent is a 1:1 mixture of methanol and hexane.
24. The process of claim 23 wherein the mixture of sertraline base and solvent is an approximately 150–200 mM solution of sertraline base in a 1:1 mixture of methanol and hexane.
25. A process for making sertraline hydrochloride Form XIV comprising the steps of:
    (a) adding sertraline hydrochloride Form II to methanol to form a suspension of solid sertraline hydrochloride in methanol;
    (b) stirring the suspension for a time sufficient to induce the transformation of sertraline hydrochloride Form II to sertraline to sertraline hydrochloride Form XIV; and
    (c) isolating sertraline hydrochloride Form XIV.

26. The process of claim 25 wherein methanol is used in an amount of from about 3 volumes per weight of sertraline hydrochloride Form II.

27. The process of claim 25 further comprising heating the isolated sertraline hydrochloride Form XIV to dry.

28. The process of claim 25 further comprising heating the suspension.

29. A process for making sertraline hydrochloride Form V comprising the steps of:
  (a) heating sertraline hydrochloride Form XIV; and
  (b) isolating sertraline hydrochloride Form V.

30. The process of claim 29 further comprising the steps of:
  (a) dissolving sertraline base in a solvent mixture comprising methanol and hexane to form a solution of sertraline base and the solvent;
  (b) adding hydrogen chloride to the solution to attain a pH of from about 0.5 to about 1.5;
  (c) precipitating sertraline hydrochloride from the solution;
  (d) removing the solvent; and
  (e) isolating sertraline hydrochloride Form XIV.

31. The process of claim 29 further comprising the preliminary steps of:
  (a) adding sertraline hydrochloride Form II to methanol to form a suspension of solid sertraline hydrochloride in methanol; and
  (b) removing the methanol to obtain sertraline hydrochloride Form XIV.

32. The process of claim 29 wherein the elevated temperature is about 80° C. and heating is continued for at least about 24 hours.

33. A process for making sertraline hydrochloride Form XIII comprising the steps of:
  (a) heating sertraline hydrochloride Form XIV; and
  (b) isolating sertraline hydrochloride Form XIII.

34. The process of claim 33 wherein the sertraline hydrochloride Form XIV is heated to about 60° C. for at least about 24 hours.

35. Sertraline hydrochloride Form XIII which is characterized by a powder X-ray diffraction pattern comprising peaks at about 8.5±0.2, 13.3±0.2, 14.0±0.2, 15.3±0.2, 16.3±0.2, 17.5±0.2, 20.1±0.2, 21.5±0.2, 22.5±0.2, 23.6±0.2, 25.0±0.2 and 25.9±0.2 degrees two-theta.

36. A process for making sertraline hydrochloride Form V comprising the steps of:
  (a) heating sertraline hydrochloride Form XV; and
  (b) recovering sertraline hydrochloride Form V.

37. The process of claim 36 wherein the sertraline hydrochloride Form XV is heated to about 80° C. for at least about 24 hours.

38. Sertraline hydrochloride Form XV which is characterized by a powder x-ray diffraction pattern comprising peaks at about 6.5±0.2, 10.7±0.2, 12.9±0.2, 14.2±0.2, 15.2±0.2, 16.6±0.2, 17.5±0.2, 18.1±0.2, 19.9±0.2, 20.4±0.2 24.0±0.2 and 24.5±0.2 degrees two-theta.

39. A process for making sertraline hydrochloride Form XV comprising the steps of
  (a) dissolving sertraline base in a solvent comprising a mixture of isopropanol and a non-polar solvent to form a solution of sertraline base,
  (b) adding aqueous hydrochloric acid to the solution of sertraline base to facilitate precipitation of sertraline hydrochloride Form XV;
  (c) removing the solvent; and
  (d) isolating sertraline hydrochloride Form XV.

40. The process of claim 39 wherein the non-polar solvent is hexane.

41. A process for making sertraline hydrochloride Form XV comprising the steps of:
  (a) adding sertraline base to isopropanol;
  (b) adding aqueous hydrochloric acid to the mixture of sertraline base and isopropanol in an amount sufficient to form sertraline hydrochloride;
  (c) heating the mixture of sertraline hydrochloride and isopropanol to facilitate complete dissolution of sertraline hydrochloride;
  (d) adding water to the mixture to facilitate complete dissolution of sertraline hydrochloride;
  (e) stirring the mixture for a time sufficient to induce the transformation to sertraline hydrochloride Form XV; and
  (f) isolating sertraline hydrochloride Form XV.

42. The process of claim 41 wherein the mixture is heated to about 60° C.

43. A process for preparing sertraline hydrochloride Form XV comprising the steps of:
  (a) forming a suspension of sertraline hydrochloride Form VI in aqueous isopropanol; and
  (b) isolating sertraline hydrochloride Form XV by removal of the aqueous isopropanol.

44. The process of claim 43 further comprising the step of heating the suspension.

45. Sertraline hydrochloride Form XVI.

46. Sertraline hydrochloride Form XVI which is characterized by a powder X-ray diffraction pattern comprising peaks at about 15.6±0.2 and 23.0°±0.20° degrees two-theta.

47. A process for preparing sertraline hydrochloride Form XVI comprising the steps of:
  (a) dissolving sertraline base in a solvent wherein the solvent is selected from the group consisting of hexane, cyclohexane and toluene to form a mixture of sertraline base and the solvent;
  (b) adding hydrogen chloride to the mixture to attain a pH of from about 1 to about 1.5;
  (c) precipitating sertraline hydrochloride Form XVI from the mixture;
  (d) removing the solvent; and
  (e) isolating sertraline hydrochloride Form XVI.

48. The process of claim 47 further comprising the step of heating the mixture to a temperature range of about 30° C. to reflux.

49. The process of claim 47 wherein the solvent is used in an amount of from about 5 to about 20 volumes per weight of sertraline base.

50. The process of claim 47 wherein the solvent is toluene.

51. The process of claim 47 wherein the solvent is cyclohexane.

52. The process of claim 47 wherein the solvent is hexane.

53. A process for preparing sertraline hydrochloride Form II comprising the steps of:
  (a) adding sertraline hydrochloride Form XIV to a solvent selected from the group consisting of ethyl acetate, acetone, and t-butyl-methyl-ether to form a suspension of sertraline hydrochloride;
  (b) heating the suspension;
  (c) stirring the suspension for a time sufficient to transform sertraline hydrochloride Form XIV to sertraline hydrochloride Form II; and
  (d) isolating sertraline hydrochloride Form II.

54. The process of claim 53 wherein the suspension is heated to a temperature range of about 25° C. to reflux.

55. The process of claim 54 wherein the suspension is heated to reflux.

56. The process of claim 53 wherein the solvent is ethyl acetate.

57. The process of claim 53 wherein the solvent is acetone.

58. The process of claim 53 wherein the solvent is t-butyl-methyl-ether.

59. The process of claim 53 further comprising the step of cooling the suspension prior to isolating sertraline hydrochloride Form II.

60. A process for preparing sertraline hydrochloride Form II comprising the steps of:
   (a) adding sertraline hydrochloride Form XV to a solvent selected from the group consisting of ethyl acetate, acetone, t-butyl-methyl-ether and cyclohexane to form a suspension of sertraline hydrochloride;
   (b) stiffing the suspension for a time sufficient to transform sertraline hydrochloride Form XV to sertraline hydrochloride Form II;
   (c) heating the suspension; and
   (d) isolating sertraline hydrochloride Form II.

61. The process of claim 60 wherein the suspension is heated to a temperature range of about 25° C. to reflux.

62. The process of claim 61 wherein the suspension is heated to reflux.

63. The process of claim 60 wherein the solvent is ethyl acetate.

64. The process of claim 60 wherein the solvent is acetone.

65. The process of claim 60 wherein the solvent is t-butyl-methyl-ether.

66. The process of claim 60 wherein the solvent is cyclohexane.

67. The process of claim 60 further comprising the step of cooling the suspension prior to isolating sertraline hydrochloride Form II.

68. The process of claim 67 wherein the suspension is cooled to a temperature range of about 25° C. to about 5° C.

69. A process for preparing sertraline hydrochloride Form II comprising the steps of:
   (a) adding sertraline hydrochloride Form XVI to a solvent selected from the group consisting of ethyl acetate and acetone to form a suspension of sertraline hydrochloride;
   (b) heating the suspension to facilitate the transformation of sertraline hydrochloride Form XVI to sertraline hydrochloride Form II; and
   (c) isolating sertraline hydrochloride Form II.

70. The process of claim 69 wherein the suspension is heated to reflux.

71. A pharmaceutical composition comprising a therapeutically effective amount of sertraline hydrochloride selected from the group consisting of: sertraline hydrochloride Form XI, Form XII, Form XIII, Form XIV, Form XV, Form XVI, and mixtures thereof.

72. A method for treating depression comprising the step of administering to a patient in need of such treatment a therapeutically effective amount of sertraline hydrochloride selected from the group consisting of: sertraline hydrochloride Form XI, Form XII, Form XIII, Form XIV, Form XV, Form XVI, and mixtures thereof.

73. A method for treating obsessive-compulsive disorder comprising the step of administering to a patient in need of such treatment a therapeutically effective amount of sertraline hydrochloride selected from the group consisting of: sertraline hydrochloride Form XI, Form XII, Form XIII, Form XIV, Form XV, Form XVI, and mixtures thereof.

74. A method for treating panic disorder comprising the step of administering to a patient in need of such treatment a therapeutically effective amount of sertraline hydrochloride selected from the group consisting of: sertraline hydrochloride Form XI, Form XII, Form XIII, Form XIV, Form XV, Form XVI, and mixtures thereof.

* * * * *